United States Patent [19]

Knobel

[11] Patent Number: 5,482,863
[45] Date of Patent: Jan. 9, 1996

[54] APPARATUS FOR SUSPENDING PARTICLES

[75] Inventor: Rolf Knobel, Rotkreuz, Switzerland

[73] Assignee: Hoffmann-La Roche Inc., Nutley, N.J.

[21] Appl. No.: 301,828

[22] Filed: Sep. 7, 1994

[30] Foreign Application Priority Data

Sep. 17, 1993 [CH] Switzerland .............. 2800/93

[51] Int. Cl.$^6$ .................. G01N 35/08
[52] U.S. Cl. .............. 436/54; 436/526; 436/180; 436/806; 422/63; 422/64; 422/65; 422/67; 422/100
[58] Field of Search .............. 422/100, 64, 65, 422/67, 63; 436/54, 526, 806, 180; 141/98, 129, 130; 73/864.25

[56] References Cited

U.S. PATENT DOCUMENTS

| | | | |
|---|---|---|---|
| 3,836,329 | 9/1974 | Jordan | 23/230 R |
| 4,632,808 | 12/1986 | Yamamoto et al. | 422/72 |
| 4,757,437 | 7/1988 | Nishimura | 364/167 |
| 4,803,050 | 2/1989 | Mack | 422/65 |
| 4,830,832 | 5/1989 | Arpagaus et al. | 422/65 |
| 5,055,263 | 10/1991 | Meltzer | 422/100 |
| 5,130,254 | 7/1992 | Collier et al. | 436/54 |
| 5,306,510 | 4/1994 | Meltzer | 422/65 |

FOREIGN PATENT DOCUMENTS

| | | |
|---|---|---|
| 131259 | 7/1984 | European Pat. Off. . |
| 9116675 | 10/1991 | European Pat. Off. . |
| 3242460 | 11/1982 | Germany . |
| 91/16675 | 10/1991 | WIPO . |

OTHER PUBLICATIONS

Derwent Abstract No. AN 85–019780/04.
Derwent Abstract No. AN 84–128468/21.

*Primary Examiner*—James C. Housel
*Assistant Examiner*—Sharidan Carrillo
*Attorney, Agent, or Firm*—George M. Gould; George W. Johnston; John P. Parise

[57] ABSTRACT

An analytical device incorporating a system for suspending particles includes a conveying device for positioning a pipetting needle at a distance from the central longitudinal axis of the reaction vessel. Particles are suspended by delivering amounts of liquid reagent to two different positions at a predetermined distance from the central longitudinal axis of a reaction vessel, such delivery generates a flow in the reaction vessel which suspends particles exclusively by injection of liquid, thus avoiding the need for subsequent shaking.

8 Claims, 3 Drawing Sheets

APPARATUS FOR SUSPENDING PARTICLES

FIELD OF THE INVENTION

The invention relates to an analytical device for suspending particles, and a method of making the suspension. Particularly, the invention is suitable for suspending magnetic microparticles during addition of reagent in a processing station for automatic DNA detections and immunoassays.

BACKGROUND OF THE INVENTION

In many methods of analysis, including immunoassays and DNA detections, a solid phase needs to be separated from a liquid phase, and subsequently washed. The last separation step in the washing process is usually followed by conveyance of the sample to a processing station (for example, an incubator) where reagent solutions are added. In the conventional method of addition, solutions are pipetted into the middle of the reagent vessel through the tip of a pipette. Reagent and solid phase must be well mixed if subsequent chemical reaction is to proceed quickly and efficiently (for example, during incubation). To thoroughly suspend the solid phase, prior art processes employ a shaking operation. Either the reaction container or the entire processing station are shaken. Such required equipment increases complexity, and thus increases the cost and total bulk of the plant. The shaking operation also disadvantageously prolongs total processing time.

The subject invention fulfills a long felt need for an apparatus and method which suspend particles without requiring an additional suspension device or shaking operation.

SUMMARY OF INVENTION

An analytical device is provided for introducing a liquid into a reaction vessel to induce mixing within the reaction vessel. The device comprises a pipetting device having conveying means for moving a pipetting needle in three directions at right angles to one another, and a processing station in which a reaction vessel having a central longitudinal axis can be disposed. The processing station is configured and dimensioned so that a defined amount of a liquid can be pipetted through the pipetting needle into the reaction vessel. The processing station is also configured and dimensioned so that the conveying means is capable of positioning the pipetting needle at a predetermined distance from the central longitudinal axis of the reaction vessel, the position of the pipetting needle relative to the reaction vessel remaining unchanged while the liquid is being pipetted.

Preferably, the pipetting needle is configured and dimensioned to be positioned in the space between the central longitudinal axis of the reaction vessel and the inner wall of the reaction vessel.

A method of suspending particles in a reaction vessel having a central longitudinal axis by introducing a volume of a liquid into the reaction vessel via a pipetting needle movable by a conveying device is also provided. The method comprises the following steps:

First, the conveying device moves the pipetting needle to a first position located at a first predetermined distance from the central longitudinal axis of the reaction vessel.

Second, the pipetting needle introduces a first predetermined volume of liquid into the reaction vessel to form a first vortex within the reaction vessel. During this step the position of the pipetting needle remains unchanged while the liquid is being introduced.

Third, the conveying device moves the pipetting needle to a second position located at a second predetermined distance from the central longitudinal axis of the reaction vessel.

Fourth, the pipetting needle introduces a second predetermined volume of liquid into the reaction vessel to form a second vortex within the reaction vessel which rotates in the opposite direction to the direction of rotation of the first vortex.

Preferably, the first position is diametrically opposite, relative to the central longitudinal axis of the reaction vessel, to the second position. The diametrically opposite wall regions, relative to the central longitudinal axis of the reaction vessel into which the liquid is being delivered, are typically those regions to which particles are already adhering. Advantageously, the particles can be magnetic microparticles.

Of great preference is the situation where the first and second predetermined distances are equal and adjacent the interior walls of the reaction vessel, and the liquid is ejected from the pipette under pressure.

DETAILED DESCRIPTION OF THE INVENTION

Figure 1:
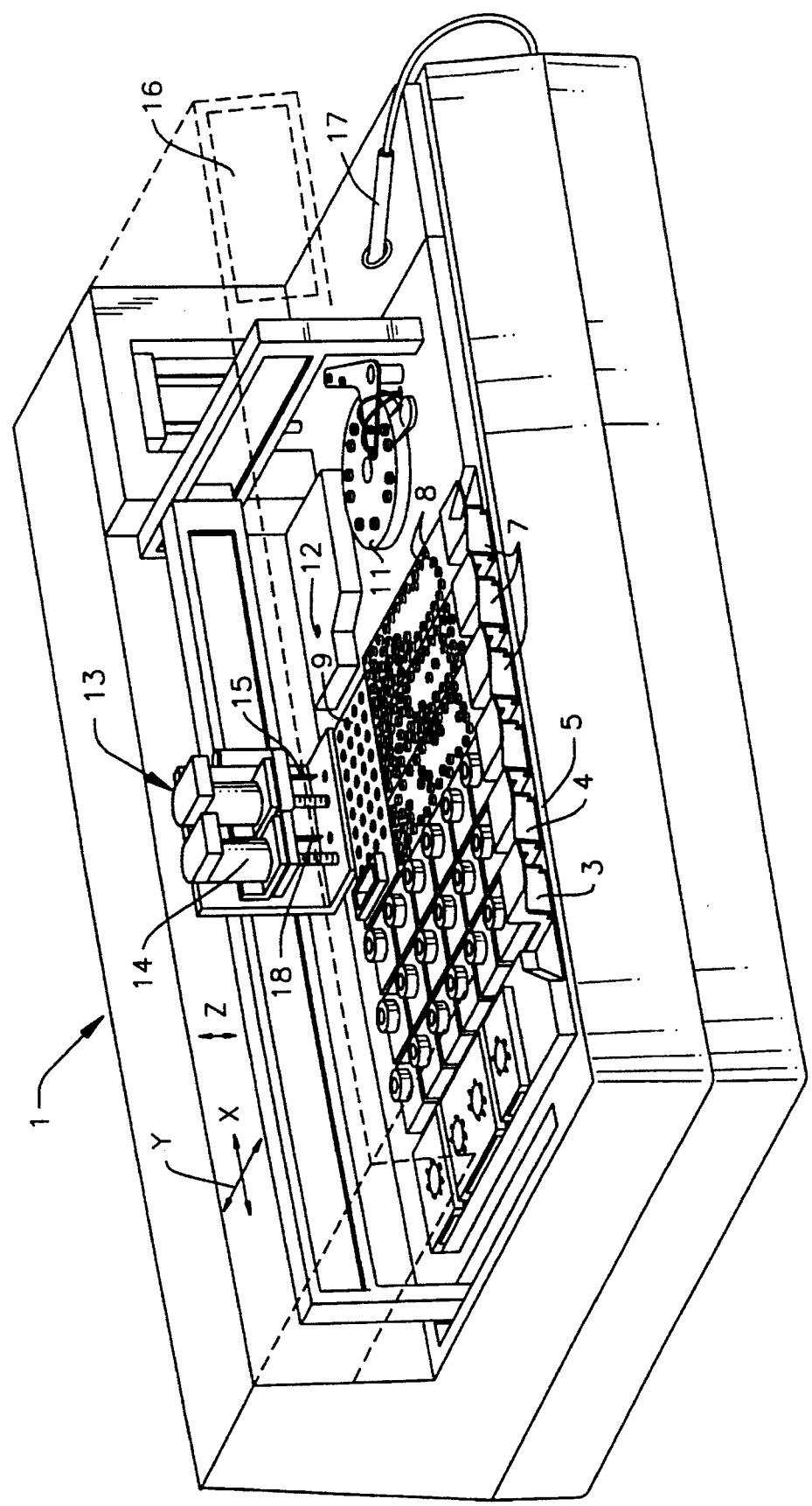
FIG. 1—A perspective view of an analytical device according to the invention.

The subject invention will now be described in terms of its preferred embodiments. These embodiments are set forth to aid in the understanding of the invention, but are not to be construed as limiting.

An aim of the present invention is to provide an analytical device and a means for suspending particles, free from the aforementioned disadvantages. The described problems are solved by an analytical device having the following components: a pipetting device with a conveying means for moving the pipetting needle in three directions at right angles to one another, at least one reaction vessel having a central longitudinal axis, the reaction vessel containing the particles to be suspended, and at least one processing station in which the reaction vessel can be disposed and on to which a defined amount of a reagent can be pipetted through the pipetting needle into the reaction vessel. The analytical device is characterized in that the conveying device is for positioning the pipetting needle at a distance from the central longitudinal axis of the reaction vessel such that the position of the pipetting needle in the reaction vessels remains unchanged while injecting the reagent.

The choice of pipetting device, reaction vessel and processing station is readily determined by a skilled artisan. Moreover, automated pipetting devices, reaction vessels and processing stations are generally well known in the art. To avoid redundancy, an intimate description of these components is not provided.

The "distance" is the region between the central longitudinal axis of the reaction vessel and the wall thereof.

Processing stations according to the invention can be stations in incubators, washing devices or the like.

Particles according to the invention may be precipitates of difficulty-soluble compounds, magnetic microparticles used as carriers in solid-phase DNA detections or immunoassays, magnetic micro-beads, or the like. Preferably the deposits are magnetic micro-beads.

Pipetting needles according to the invention are preferably designed so that a reaction container cover can be pierced.

Another aim of the invention is to provide a method whereby particles can be suspended without the previously described disadvantages, by introducing a defined amount of a liquid into a reaction vessel.

The present invention provides method of suspending particles in a reaction vessel. A predetermined volume of a reagent liquid is introduced into the reaction vessel by a pipetting needle which is movable by a conveying device. The conveying device brings the pipetting needle to a first position at a first distance from the central longitudinal axis of the reaction vessel. Once the pipetting needle is at the first position, some of the predetermined volume of reagent liquid is injected into the reaction vessel and forms a first vortex (the position of the pipetting needle in the reaction vessel remains unchanged while injecting the reagent liquid). The conveying device then moves the pipetting needle to a second position at a second distance from the central longitudinal axis of the reaction vessel, and when the pipetting needle is at the second position, the remaining part of the predetermined volume of the reagent liquid is injected into the reaction vessel, forming a second vortex which rotates in the opposite direction to the rotation of the first vortex. Typically, the first and second distances are equal in o opposite directions from the central longitudinal axis of the reaction vessel. However, the first and second distances need not be exactly equal and may be varied to conform with differing tube sizes and configurations.

The particles can adhere to diametrically opposite wall regions of the reaction vessel, relative to the central longitudinal axis. This is the case e.g. when the particles are magnetic microparticles and the solid and liquid phase are first separated by two diametrically opposite magnets.

The inventive process is suitable for other applications in addition to suspending particles deposited at diametrically opposite regions on the wall, relative to the central longitudinal axis. After a portion of the predetermined volume of reagent liquid has been pipetted into the reaction vessel in a first position, the pipetting needle can be rotated to any desired second position at a distance from the central longitudinal axis of the reaction vessel, where the deposited particles are suspended by adding the remaining part-volume of reagent liquid. In addition, a solution already in the reaction vessel can be efficiently mixed with other solutions.

A main advantage of the present invention is that addition of reagent liquid at two different positions in a reaction vessel results in a flow therein, enabling the solid phase to be suspended exclusively by injection of reagent, thus avoiding the need for a subsequent shaking operation. In analytical equipment, the inventive device can produce an optimum suspension of particles during the addition of reagent, simply by choosing a suitable program for actuating the pipetting needle, so that a maximum number of samples can be processed per unit time.

By way of example, the drawings show an analytical device for automatic solid-phase DNA detections in which the solid phase consists of magnetic microparticles, and the solid and liquid phases are separated by permanent magnets. After separation, the microparticles are deposited on two diametrically opposite wall regions of the reaction vessel.

FIG. 1 shows an analytical device 1 designed for, among other things, performing DNA detections. The device 1 contains means for performing the aforementioned DNA detections, in the present case two racks 3, 4 with reagents on a vibrating table 5, three racks 7 holding throwaway (disposable) reagent containers 8, a temperature-controlled incubator 9, a washing device 11 and a photometer 12.

Samples, reagents and reagent vessels are conveyed by a conveying device 13 movable in an x-y coordinate system. Conveying device 13 comprises a pipetting means 14 with a pipetting needle 18 and a reaction vessel gripper 15, both movable in the z direction.

To transfer a reagent, the pipetting needle 18 is moved towards a rack 3, 4, where a reagent is withdrawn by suction. The pipetting needle 18 is then moved to a reagent vessel 8, where the reagent is delivered. Process parameters can be input via a control panel 16 and/or a bar code wand 17. The CPU controls and coordinates all operations in the process.

FIGS. 2–5 show the method according to the invention for suspending magnetic microparticles.

Figure 2:
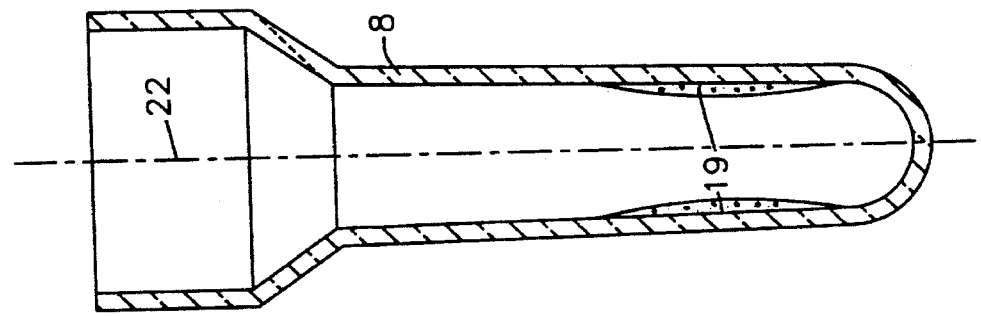

FIG. 2 shows a reaction vessel 8 having a central longitudinal axis 22. The particles 19 adhere to diametrically opposite inner walls of the reaction vessel 8, relative to the central longitudinal axis 22.

Figure 3:
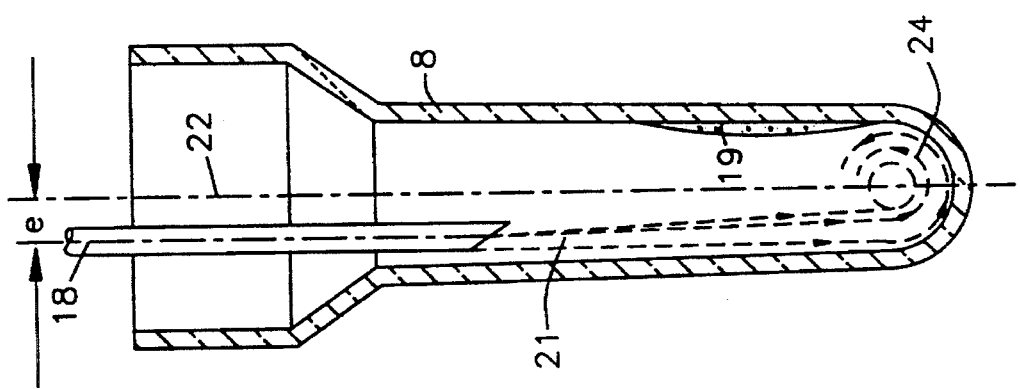

FIG. 3 shows the pipetting needle 18 in a first position at a distance e from the central longitudinal axis 22, where a part of the predetermined volume of reagent liquid 21 is injected. The resulting vortex 24 is diagrammatically shown.

Figure 4:
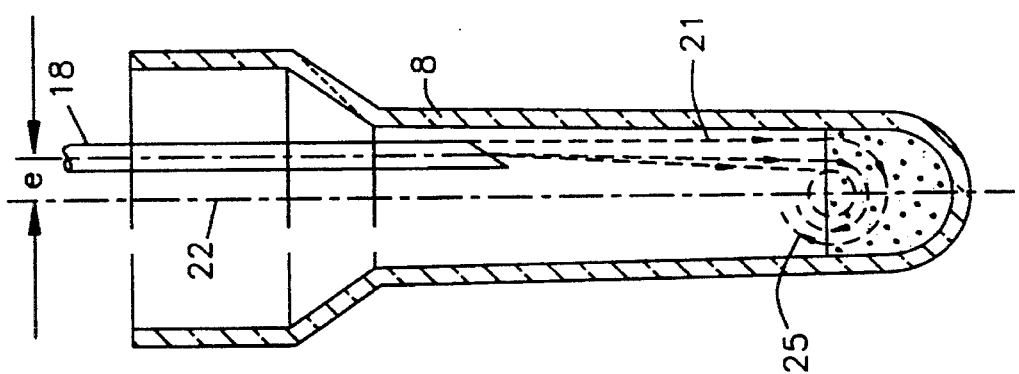

FIG. 4 shows the pipetting needle 18 in the second position at a distance e from the central longitudinal axis 22, where the rest of the predetermined volume of reagent liquid 21 is injected. The resulting vortex 25 is diagrammatically indicated, showing the reverse direction of rotation.

Figure 5:
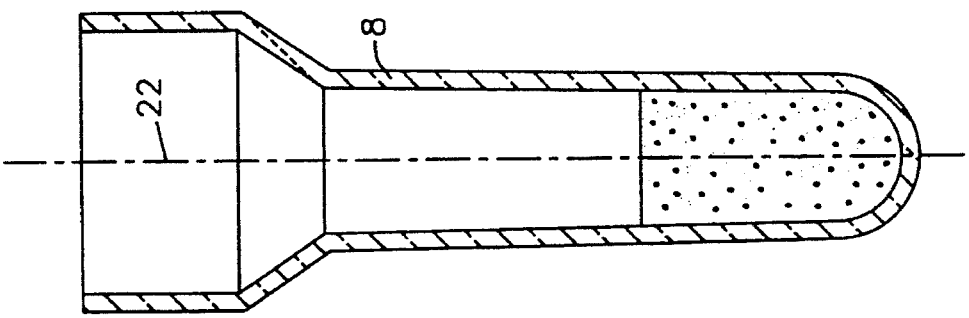
FIGS. 2–5—Illustration depicting the subject process for suspending particles.

FIG. 5 is a diagram of resuspended particles. The pipetting needle 18 can be adjusted in simple manner by a conveying device 13, using a suitable control program (x-y adjustment).

Figure 6:
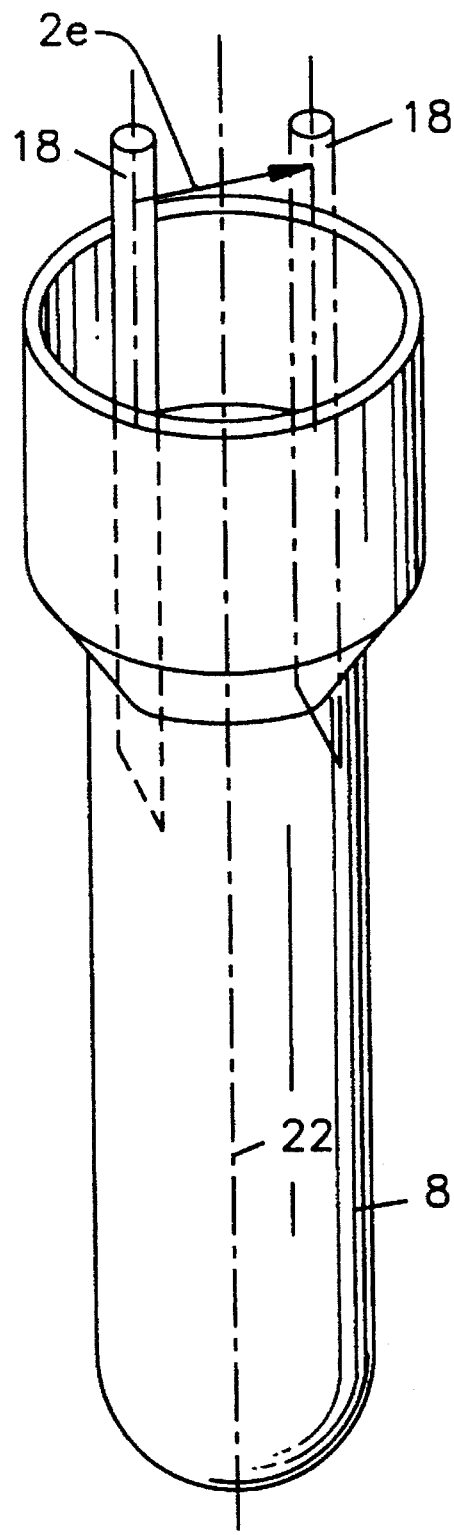
FIG. 6—A axonometric diagram of the pipette guidance according to the invention, as per FIGS. 2 to 5.

FIG. 6 shows the linear movement of the pipetting needle 18 at two diametrically opposite positions relative to the central longitudinal axis 22. The total travel is 2e.

Figure 7:
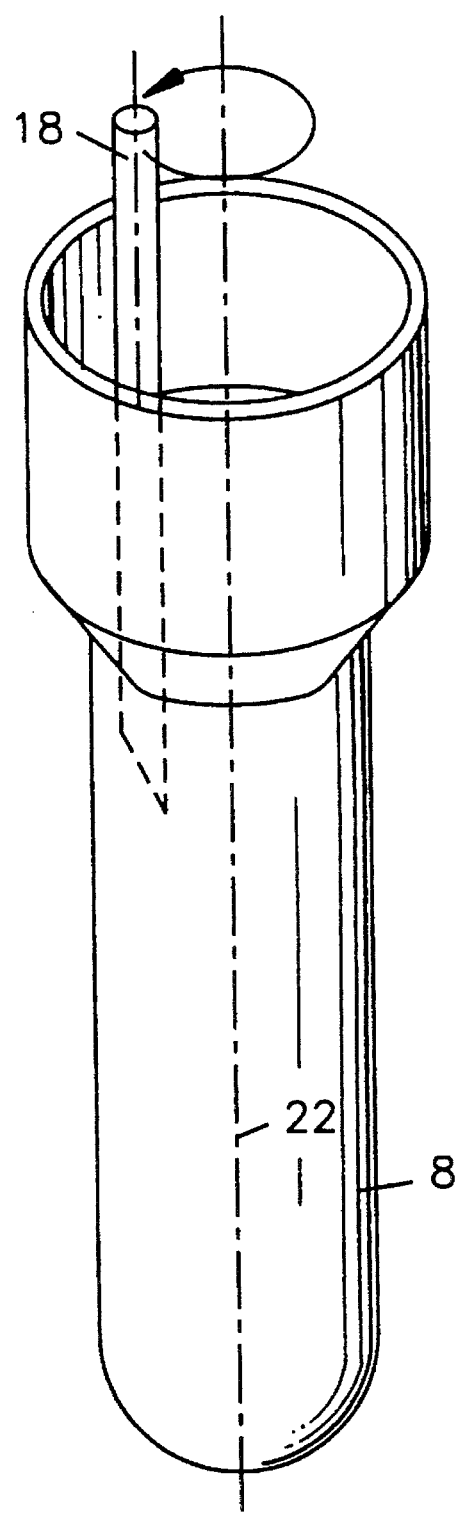
FIG. 7—An alternate method of guiding a pipette according to the invention.

FIG. 7 shows rotating movement of the pipetting needle 18 at any desired positions at a distance e from the central longitudinal axis 22.

The invention has been described in terms of its preferred embodiments. However, upon reading the present specification various alternative embodiments will become obvious to those skilled in the art. For example, travel distance (e) can be readily varied, as can the type of pipetting device, type of reaction container, processing station, etc. The movement from the first predetermined pipetting position to the second predetermined pipetting position could also be effected by moving the processing station, as opposed to by moving the pipetting needle itself. These variations are to be considered within the scope and spirit of the subject invention which is only to be limited by the claims which follow and their equivalents.

What is claimed is:

1. An analytical device for suspending particles in a reaction vessel, which comprises:

(a) a processing station into which a reaction vessel can be disposed;

(b) a pipetting device having conveying means for moving a pipetting needle in three directions at right angles to one another, and (c) programmable means for controlling the position of the pipetting needle relative to the processing station so as to cause the pipetting needle to dispense predetermined volumes of liquid at more than one distinct location within the reaction vessel when disposed at the processing station, the position of the pipetting needle relative to the reactor vessel remaining unchanged at each location while liquid is being dispensed into the reaction vessel when disposed at the processing station.

2. The device according to claim 1, wherein the reaction vessel has an inner wall and a central longitudinal axis, and the programmable means causes the pipetting needle to dispense liquid into the reaction vessel at a location between the inner wall and the central longitudinal axis when the reaction vessel is disposed at the processing station.

3. The device according to claim 1, wherein the pipetting device dispenses the liquid with a force sufficient to generate a vortex within the reaction vessel.

4. The device according to claim 2 wherein the pipetting needle is configured and dimensioned to be positioned in the space between the central longitudinal axis of the reaction vessel and the inner wall of the reaction vessel.

5. An analytical device for suspending particles in a reaction vessel having an inner wall and a central longitudinal axis, which comprises:

(a) a processing station into which a reaction vessel can be disposed;

(b) a pipetting device having conveying means for moving a pipetting needle in three directions at right angles to one another, and (c) programmable means for controlling the position of the pipetting needle relative to the processing station so as to cause the pipetting needle to dispense predetermined volumes of liquid at a location between the inner wall and the central longitudinal axis of the reaction vessel when disposed at the processing station, the position of the pipetting needle relative to the reactor vessel remaining unchanged at each location while liquid is being dispensed into the reaction vessel when disposed at the processing station.

6. The device according to claim 5, wherein the programmable means causes the pipetting needle to dispense liquid at a plurality of locations within the reaction vessel when disposed at the processing station.

7. The device according to claim 5, wherein the pipetting device dispenses the liquid with a force sufficient to generate a vortex within the reaction vessel.

8. The device according to claim 5, wherein the pipetting needle is configured and dimensioned to be positioned in the space between the central longitudinal axis of the reaction vessel and the inner wall of the reaction vessel.

* * * * *